(12) United States Patent
Golijanin et al.

(10) Patent No.: US 9,089,601 B2
(45) Date of Patent: Jul. 28, 2015

(54) PRE- AND INTRA-OPERATIVE IMAGING OF BLADDER CANCER

(75) Inventors: Dragan Golijanin, Rochester, NY (US); Edward M. Messing, Rochester, NY (US); Jay E. Reeder, East Rochester, NY (US); Ronald Wood, Rochester, NY (US); Aimee Johnson, Webster, NY (US)

(73) Assignee: University of Rochester, Rochester, NY (US)

( * ) Notice: Subject to any disclaimer, the term of this patent is extended or adjusted under 35 U.S.C. 154(b) by 2004 days.

(21) Appl. No.: 11/775,037

(22) Filed: Jul. 9, 2007

(65) Prior Publication Data

US 2008/0125650 A1 May 29, 2008

Related U.S. Application Data

(60) Provisional application No. 60/819,971, filed on Jul. 10, 2006.

(51) Int. Cl.
*A61B 6/00* (2006.01)
*A61K 49/00* (2006.01)
*A61K 35/26* (2015.01)

(52) U.S. Cl.
CPC ............... *A61K 49/0034* (2013.01); *A61B 6/00* (2013.01); *A61K 35/26* (2013.01); *A61K 49/0032* (2013.01); *A61K 49/0043* (2013.01)

(58) Field of Classification Search
CPC . A61B 6/00; A61K 49/0034; A61K 49/0032; A61K 4/0043; A61K 5/269

USPC .................................................. 600/431, 473
See application file for complete search history.

(56) References Cited

U.S. PATENT DOCUMENTS

| | | | |
|---|---|---|---|
| 6,351,663 B1 | 2/2002 | Flower et al. | |
| 6,482,837 B1 | 11/2002 | Wood | |
| 6,797,704 B2* | 9/2004 | Leong et al. | 514/44 R |
| 6,804,549 B2 | 10/2004 | Hayashi | |
| 6,905,884 B2* | 6/2005 | Grissom et al. | 436/503 |
| 7,381,400 B2* | 6/2008 | Woltering | 424/9.1 |
| 2002/0111502 A1* | 8/2002 | Engler et al. | 552/550 |
| 2003/0187319 A1* | 10/2003 | Kaneko et al. | 600/9 |
| 2003/0187349 A1 | 10/2003 | Kaneko et al. | |
| 2003/0232016 A1 | 12/2003 | Heinrich | |
| 2004/0082863 A1* | 4/2004 | McGreevy et al. | 600/476 |
| 2007/0276257 A1* | 11/2007 | Heanue et al. | 600/476 |

FOREIGN PATENT DOCUMENTS

WO    WO 2004/085676 A1    7/2004

OTHER PUBLICATIONS

Alec M. Grand and Jahn V. Frangioni, M.D.; "An Operational near-infrared fluorescence imaging system prototype for large aniaml surgery;" Dec. 2003; Technology in Cancer Resarch and Treatment; vol. 2, No. 6; ISSN 1533-0346.*

(Continued)

*Primary Examiner* — Vani Gupta
(74) *Attorney, Agent, or Firm* — Patent Technologies, LLC; Robert D. Gunderman, Jr.

(57) ABSTRACT

The invention provides methods for visualizing and distinguishing sentinel lymph nodes and involved nodes from other lymph nodes in the vicinity of the bladder in patients undergoing cystectomy or other operations to remove bladder tumors.

10 Claims, 1 Drawing Sheet

(56) References Cited

OTHER PUBLICATIONS

Deborah W. Knapp, Larry G. Adams, Jacqueline D. Niles, Michael D. Lucroy, Jose Ramos-Vara, Patty L. Bonney, Amalie E. deGortari, and John V. Frangioni; "Near infrared imaging to identify sentinel lymph nodes in invasive urinary bladder cancer;"—Feb. 22, 2006 as per online publication; Proc. SPIE 6078, 607838 (2006), DOI:10.1117/12.646822.*

Amir Sherif, Ulrike Garske, Manual de la Torre, and Magnus Thorn; "Hybrid SPECT-CT: An Additional technique for sentinel node detection of patients with invasive bladder cancer;" Mar. 20, 2006; European Association of Urology; doi:10.1016/j.eururo.2006.03.002; pp. 83-91.*

De Grand, A.M. and J.V. Frangioni, "An operational near-infrared fluorescence imaging system prototype for large animal surgery," 2003, *Technology in Cancer Research & Treatment*, vol. 2(6), pp. 1-10.

Demos, S.G., et al., "Near-infrared autofluorescence imaging for detection of cancer," 2004, *J. Biomed. Opt.*, vol. 9(3), pp. 587-592.

Frangioni, John V., "In vivo near-infrared fluorescence imaging," 2003, *Current Opinion in Chemical Biology*, vol. 7, pp. 626-634.

Haglund, M.M., et al., "Enhanced optical imaging of rat gliomas and tumor margins," 1994, *Neurosurgery*, vol. 35(5), pp. 930-941.

Herts, Brian R., "Imaging for renal tumors," 2003, *Curr. Opin. Urol.*, vol. 13, pp. 181-186.

Humblet, V., et al., "High-affinity near-infrared fluorescent small-molecule contrast agents for in vivo imaging of prostate-specific membrane antigen," 2005, *Mol. Imaging*, vol. 4(4), pp. 448-462.

Kim, S., et al., "Near-infrared fluorescence type II quantum dots for sentinel lymph node mapping," 2004, *Nature Biotechnology*, vol. 22(1), pp. 93-97.

Leissner, J., et al., "Extended radical lymphadenectomy in patients with urothelial bladder cancer: Results of a prospective multicenter study," 2004, *J. Urol.*, vol. 171, pp. 139-144.

Liedberg, F., et al., "[Bladder cancer and the sentinel node concept,]" 2003, *Aktuelle Urol.*, vol. 34(2), pp. 115-118.

Liedberg, F., et al., "Intraoperative sentinel node detection improves nodal staging in invasive bladder cancer," 2006, *J. Urol.*, vol. 175, pp. 84-89.

Malmström, P-U, et al., "Early metastatic progression of bladder carcinoma: molecular profile of primary tumor and sentinel lymph node," 2002, *J. Urol.*, vol. 168, pp. 2240-2244.

Malmström, P-U, et al., "Re: Extended radical lymphadenectomy in patients with urothelial bladder cancer: Results of a prospective multicenter study," 2004, *J. Urol.*, vol. 172, p. 386.

Marangos, N., et al., "In vivo visualization of the cochlear nerve and nuclei with fluorescent axonal tracers," 2001, *Hearing Research*, vol. 162, pp. 48-52.

Nakayama, A., et al., "Functional near-infrared fluorescence imaging for cardiac surgery and targeted gene therapy," 2002, *Mol. Imaging*, vol. 1(4), pp. 365-377.

Nimura, H., et al., "Infrared ray electronic endoscopy combined with indocyanine green injection for detection of sentinel nodes of patients with gastric cancer," 2004, *British Journal of Surgery*, vol. 91, pp. 575-579.

Parungo, C.P., et al., "In vivo optical imaging of pleural space drainage to lymph nodes of prognostic significance," 2004, *Annas of Surgical Oncology*, vol. 11(12), pp. 1085-1092.

Parungo, C.P., et al., "Intraoperative identification of esophageal sentinel lymph nodes with near-infrared fluorescence imaging," 2005, *J. Thorac. Cardiovasc. Surg.*, vol. 129, pp. 844-850.

Sherif, A., et al., "Lymphatic mapping and detection of sentinel nodes in patients with bladder cancer," 2001, *J. Urol.*, vol. 166, pp. 812-815.

Soltesz, E.G., et al., "Intraoperative sentinel lymph node mapping of the lung using near-infrared fluorescent quantum dots," 2005, *Ann. Thorac. Surg.*, vol. 79, pp. 269-277.

Uren, Roger F., "Cancer surgery joins the dots," 2004, *Nature Biotechnology*, vol. 22(1), pp. 38-39.

Author Unknown, "IC-Green (Indocyanine Green for Injection, USP)," Nov. 2008, 2 pp., Akorn, Inc., Lake Forest, IL, USA.

* cited by examiner

PRE- AND INTRA-OPERATIVE IMAGING OF BLADDER CANCER

CROSS-REFERENCES TO RELATED APPLICATIONS

This application claims priority to U.S. Provisional Application 60/819,971, filed Jul. 10, 2006, the contents of which are hereby incorporated by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The American Cancer Society estimated that, in 2006, over 60,000 Americans would develop cancer of the urinary bladder, and that over 13,000 Americans would die of it. Bladder cancer is the fourth most common cancer in American men, and the eighth most common in women. The U.S. National Cancer Institute ("NCI") estimated that, of the 60,000 who were expected to develop the disease in 2006, 70 to 80% of the patients would be diagnosed with superficial bladder tumors, that is, tumors staged at stage Ta, Tis, or T1. Such early stage tumors can usually be successfully treated by transurethral resection of the bladder, with follow up by cystoscopy (that is, visualization of the interior surface of the bladder through a cystoscope introduced through the urethra) to detect whether tumors recur following removal of the first. The remaining patients present with more invasive tumors. Some 50% of these patients have muscle-invasive disease and have their bladders removed, which is known as radical cystectomy.

According to the NCI, invasive tumors that are confined to the bladder muscle on pathologic staging after radical cystectomy are associated with approximately a 75% 5-year progression-free survival rate. Patients with more deeply invasive tumors, which are also usually less well differentiated, and those with lymphovascular invasion experience 5-year survival rates of 30% to 50% following radical cystectomy. When the patient presents with locally extensive tumor that invades pelvic viscera or with metastases to lymph nodes or distant sites, 5-year survival is uncommon. Thus, determining the extent to which tumor cells have spread to lymph nodes is important in determining the patient's prognosis.

Lymph nodes which receive drainage from a cancerous organ are known as sentinel lymph nodes. As described by Roger Uren, Nature Biotech, 22:38-9 (2004), "[l]ymphatic drainage is mapped from a primary tumor site to the draining lymph node or nodes, and these are then removed for detailed histological examination. If the sentinel node is normal, all of the lymph nodes in the node field can be assumed to be normal." Sentinel lymph node (for convenience, sometimes referred to herein as "sentinel node" or "SLN") biopsies therefore can permit sparing other lymph nodes which may be present in the pelvic area, reducing trauma to the patient while maintaining or improving prognosis. As Uren further notes, however, such biopsies are very difficult to perform accurately in patients. Thus, methods of accurately identifying sentinel lymph nodes are of great interest.

Several methods have been explored for detecting sentinel nodes in patients with bladder cancer. The histopathological status of the identified SLNs was diagnostic for all other excised lymph nodes. Sentinel nodes often seem to be located outside the obturator lymphatic field, which is normally examined during preoperative staging of bladder cancer. (Sherif et al., *J Urol.*, 165(3):812-815 (2001)). Liedberg et al., *Aktuelle Urol*, 34(2): 115-118 (2003) studied 28 patients scheduled for cystectomy using preoperative lymphoscintigraphy, perioperative dye detection (Patent Blue) and dynamic lymphoscintigraphy. The substances were injected adjacent to the tumor in the detrusor muscle. Sentinel nodes were detected in 21 of 26 of the investigated patients. Seven of 21 SLN were located outside the obturator fosse. Of the eight patients with lymph node metastasis, five displayed metastasis in lymph nodes outside the obturator fossa. There was one false negative SLN in a patient with multifocal tumor, while in the other seven patients with lymph node metastasis, these were detected in the SLN. The authors concluded that sentinel node detection is possible in most cases of bladder cancer scheduled for cystectomy. In their updated series, Liedberg et al. reported that, in 75 patients, 81% had SLNs detected. (Liedberg et al., *J Urol.*, 175(1):84-88 (2006)). Of the 32 lymph node positive cases 26 (81%) had a positive (metastatic) SN. Thus, the false-negative rate was 6 of 32 cases (19%). Five false-negative cases had macrometastases and/or perivesical metastases. In 9 patients (14%), the SLN contained micrometastases (less than 2 mm), in 5 of whom the micrometastasis was the only metastatic deposit. Thus, this method had a relatively high rate of false-negatives.

A variety of medical techniques have been used for imaging biological tissues and organs. These include traditional x-rays, ultra-sound, magnetic resonance imaging ("MRI"), and computerized tomography ("CT"). Techniques such as MRI, micro-CT, micro-positron emission tomography ("PET"), and single photon emission computed tomography ("SPECT") have been explored for imaging function and processes in small animals or in vivo, intra operatively. These technologies offer deep tissue penetration and high spatial resolution, but are costly and time consuming to implement.

Several new, nanoparticle systems for imaging sentinel lymph nodes are in development. One of these new systems uses so-called "dendrimers", or spherical polymers, to carry agents such as the MRI contrast agent gadolinium to visualize nodes. In another, "nanocrystals," or "quantum dots," made of silicon or similar materials, can be "tuned" to fluoresce in the near infrared.

It would be desirable to have additional methods for imaging sentinel lymph nodes of bladder cancer patients undergoing radical cystectomy or other procedures for aggressive or advanced disease.

BRIEF DESCRIPTION OF THE DRAWINGS

FIG. 1A shows the bladder of a mouse being instilled with the dye indocyanine green. FIG. 1B shows the fluorescing of the mouse's lymphatic channels and nodes on iliac bifurcation following instillation of the dye into the bladder. FIG. 1C shows fluorescing of a lymph node excised following instillation of the dye into the bladder.

DETAILED DESCRIPTION OF THE INVENTION

Introduction

Figure 1A:
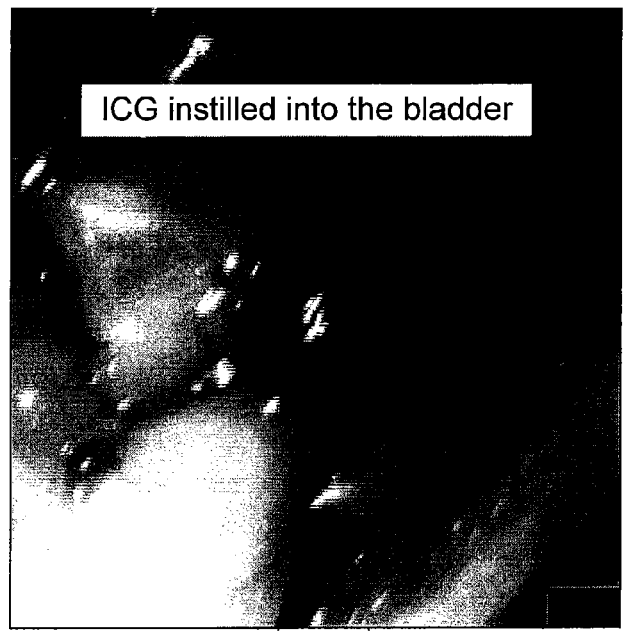
FIGS. 1A-C.
Figure 1B:
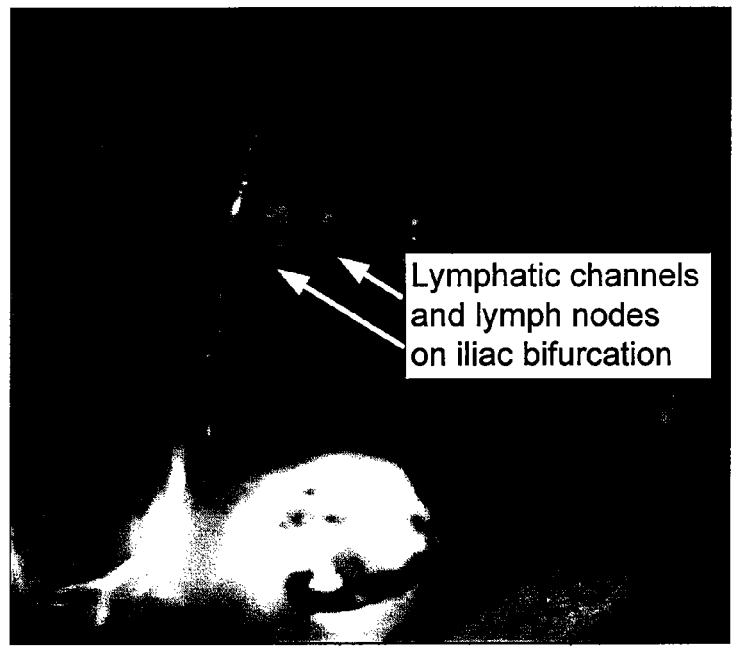
Figure 1C:
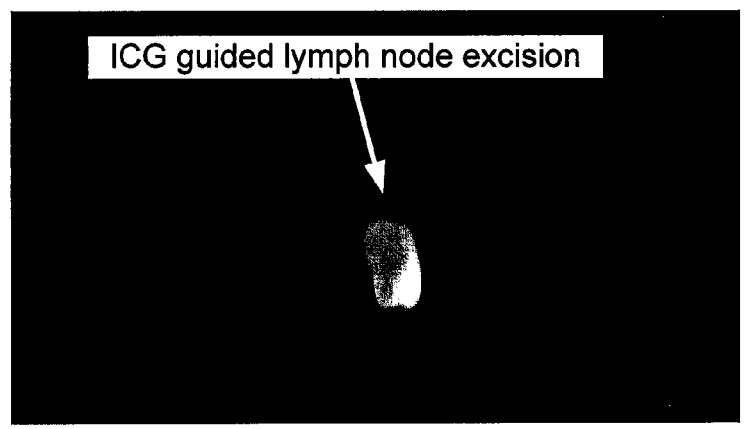

The present invention provides new methods for detecting sentinel lymph nodes (sometimes referred to herein as "SLN") in patients with urinary bladder cancer. In patients with invasive bladder cancer, the histological status of regional lymph nodes is one of the most important and reliable survival predictors. The tumor status of SLN can reflect that of the regional lymph nodes. This may be accomplished with the intravesical administration of a non-toxic fluorescent dye, such as indocyanine green.

Surprisingly, we have found that the dye can be administered simply by instillation into the lumen of the bladder, rather than being injected into the tumor or the bladder wall (injection into the wall of an organ having a lumen is generally referred to as an "intramural" injection), as is generally required by other methods, such as the use of fluorescent quantum dots. This may be viewed as particularly surprising as the bladder may be thought of as being designed to contain liquid and further in view of the fact that urine is not known to drain through the lymphatic channels serving the bladder. Installation into the lumen (intravesical administration) is both easier and faster than intramural injection. Conveniently, the dye may be instilled into the lumen through a cystoscope (an endoscope), a catheter, or a like device. Conversely, a practitioner who prefers to introduce the dye by an intramural injection can introduce the dye to the bladder using, for example, a rigid cystoscope with a needle. Typically, the tumor is imaged when making the injection or injections through standard endoscopic techniques. Thus, the invention extends the methods available to the practitioner for identifying sentinel lymph nodes, and allows identification of sentinel nodes in all landing zones of bladder drainage, decreases morbidity associated with the procedure and speeds the intraoperative identification of sentinel and involved lymph nodes.

When instilled into the lumen, the dye is then taken up by the bladder, and flows from the bladder through lymphatic vessels to the sentinel nodes, which can then be identified by their fluorescence. Likewise, when introduced by intramural injection, the dye flows from the bladder through lymphatic vessels to the sentinel nodes, which can then be identified by their fluorescence upon excitation of the dye by light of the appropriate frequency. In animal studies, SNL could be visualized in animals in which dye was instilled at 10, 20, 30, or 60 minutes prior to intraoperative detection.

Laparoscopic lymph node dissection is more difficult than open dissection surgeries, and the nodes are in close proximity to large pelvic vessels. Any injury to these vessels would lead to conversion of laparoscopic to open surgery. Because of these risks, laparoscopic lymph node dissections are much more limited in number of resected nodes than open procedures. Standard lymph node dissection is performed in laparoscopic surgeries; the extent of dissection does include common, external, internal iliac and obturator nodes.

During laparoscopy, there is an increased risk of injury to lower extremity vessels and conversion of the procedure to an open one. The methods of the present invention increase the accuracy and sensitivity of detecting SLN with minimal false negatives, and are expected to reduce the incidence of vascular injuries, significantly shorten surgical procedures, and decrease delayed morbidity in comparison to currently available techniques. In cases where lymph node mapping reveals an unusual SLN anatomical pattern, this approach may also improve cancer specific survival after SLN removal.

As persons of skill appreciate, fluorescent dyes typically have a known excitation frequency and a known emitting frequency. After sufficient time has elapsed to permit the dye to flow through the lymphatic vessels to the nodes draining the bladder, a light source capable of emitting light of the dye's excitation frequency is positioned in proximity to the bladder so as to permit light from the light source to illuminate the area around the bladder or chosen areas around the bladder in an amount sufficient to excite the dye. A camera or other device capable of capturing an image of light received at the emission frequency of the dye is positioned to receive light emitted from dye in lymph nodes in the area of interest.

Conveniently, the light goes through a filter capable of selectively passing light in the dye's emission frequency while blocking light at the dye's excitation frequency, thus permitting the receiving device to provide an image based on emission light from the dye.

In some embodiments, the dye used is indocyanine green, or "ICG." After intravenous injection, ICG is bound within 1 to 2 seconds, mainly to globulins (1-lipoproteins), and remains intravascular, with normal vascular permeability. ICG is not metabolized in the body and is excreted exclusively by the liver, with a plasma half-life of 3 to 4 minutes. Thus, ICG is available almost immediately after injection for visualization of lymph nodes in the area of interest.

The prompt and accurate determination of whether a lymph node in the area of interest is a sentinel lymph node reduces both the need to remove other lymph nodes near the bladder and to subject them to review by a pathologist. This not only reduces the trauma to the patient and ancillary damage to the patient's lymphatic system, but also reduces the time for the overall operation, since it avoids the need for the pathologist to examine every lymph node in the pelvic area to determine whether the tumor has released metastatic cells.

Instrumentation

For convenience, the following discussion will refer to instrumentation optimized for use with the exemplar dye ICG. Persons of skill are, of course, aware of the excitation and emission frequencies of other fluorescent dyes and can adjust the device as needed for use with respect to other dyes as desired.

Conveniently, the instrumentation used for visualization of the lymph nodes in the area of interest comprises both a laser and an imaging system. For use with ICG, for example, the laser preferably consists of a laser diode providing a maximum of 3 W output at 806 nm. For other dyes, the laser diode is selected to provide a light with a wavelength at an excitation frequency appropriate for the dye selected. For convenience of reference, the discussion below refers to the exemplar dye ICG. Persons of skill will recognize that the other dyes mentioned herein as suitable for use in the inventive methods and procedures could be substituted for ICG, with the light source selected or adjusted to provide illumination optimized for the excitation frequency suitable for the particular dye chosen. The device for capturing the light emitted by the dye is in turn selected for the ability to receive light of the appropriate frequency, or adjusted to be able to do so.

The laser output is decollimated (i.e. optics are used to spread out the laser light from a tight beam) to provide even illumination over a field of view, for example, 7.6 cm by 7.6 cm at a working distance of 30 cm. The imaging system typically has a camera containing a charge-coupled device ("CCD") or a complementary symmetry metal oxide semiconductor ("CMOS") image sensor sensitive into the near infrared spectrum and, for use with ICG, is equipped with an 815 nm edge filter. In some embodiments, the laser or camera or both, are supported by an articulated arm connected to a wheeled base. This allows the imaging head to be moved into close proximity to the surgical table and for vertical movement of the head to attain an appropriate focal distance above the area of interest. The imaging head and extension arm that protrudes over the surgical field are typically covered with an optically transparent sterile drape. The laser can conveniently be activated by means of a computer command or by foot pedal. Laser/camera devices suitable for intra-operative imaging are commercially available. In some preferred embodiments, the laser/camera device is a SPY® Intra-operative Imaging System, a HELIOS® Imaging System, or a LUNA® Imaging System (all by Novadaq Technologies, Inc., Mississauga, Ontario, Canada).

In some embodiments, an instrument having an optical configuration similar to a fluorescence microscope may be used, in which a dichroic mirror is used to split the paths of the illumination (the excitation light). The excitation light reflects off the surface of the dichroic mirror into the objective, while the fluorescence emission passes through the dichroic mirror to the eyepiece or is converted into a signal to be presented on a screen. The instrument may further have an excitation filter or an emission filter, or both, to select the wavelengths appropriate for each function. Conveniently, the filters are interference filters, which block transmission of frequencies out of their bandpass.

For immediate observation, ICG is administered intravenously and as the dye passes through the vessels, the 806 nm light causes the dye to fluoresce, emitting light at 830 nm. For visualizing lymph nodes in the area of interest, the ICG is administered, allowed to accumulate at the area of interest and then is exposed to light at 806 nm. The emitted light is then captured using the imaging system. As noted, the capture system is typically a video camera containing a CCD or CMOS image sensor. The capture system feeds the image to a monitor so that the surgeon can visualize the fluorescence of the dye in lymph nodes in the area of interest in real time. Filters limit the light detected to a range appropriate for the selected fluorescence wavelengths. Optionally, the camera is also attached to a computer and the image is saved, which not only permits documentation of the lymph nodes in the area of interest, but also can be used for training urologic surgeons, nurses, and other medical staff. Typically, the time required for positioning the device is 2 minutes, while the total time that the vessels are illuminated with laser light is 30 seconds.

The methods described herein are suitable for use in mammals. Examples of suitable mammals include, but are not limited to, humans, non-human primates, dogs, cats, sheep, cows, pigs, horses, mice, rats, rabbits, and guinea pigs. Use in humans and primates, and particularly in humans, is preferred.

Dyes for Visualization

As persons of skill are aware, fluorescent dyes have a particular excitation wavelength which causes the dye to fluoresce and emit light of a particular emission wavelength. Persons of skill will appreciate that considerable literature is available in the art on the characteristics of different dyes, including their excitation wavelength and emission wavelength. This literature is well known and will not be set forth in detail herein.

The dye is imaged by exciting it with a light that has an excitation wavelength appropriate for the particular dye used. Persons of skill are aware that a variety of dyes exist, and that each dye has an excitation wavelength and an emission wavelength. Some dyes, for example, fluoresce under ultraviolet ("UC") illumination while others fluoresce under incandescent illumination. The literature on the use of fluorescent dyes and probes in biological assays includes, for example, Dewey, T. G., Ed., Biophysical and Biochemical Aspects of Fluorescence Spectroscopy, Plenum Publishing (1991), Guilbault, G. G., Ed., Practical Fluorescence, Second Edition, Marcel Dekker (1990), Lakowicz, J. R., Ed., Topics in Fluorescence Spectroscopy: Techniques (Volume 1, 1991); Principles (Volume 2, 1991); Biochemical Applications (Volume 3, 1992); Probe Design and Chemical Sensing (Volume 4, 1994); Nonlinear and Two-Photon Induced Fluorescence (Volume 5, 1997); Protein Fluorescence (Volume 6, 2000); DNA Technology (Volume 7, 2003); Plenum Publishing, and Lakowicz, J. R., Principles of Fluorescence Spectroscopy, Second Edition, Plenum Publishing (1999) and W. T. Mason, ed., Fluorescent and Luminescent Probes for Biological Activity. A Practical Guide to Technology for Quantitative Real-Time Analysis, Academic Press (Second Ed., 1999).

Preferred fluorescent dyes suitable for use in the methods of the invention are non-toxic dyes which fluoresce when exposed to radiant energy, e.g. light. Preferably, the dyes are near infrared fluorochromes, or "NIRF" that emit light in the near infra red spectrum. In some embodiments, the dye is a tricarbocyanine dye, and in particularly preferred embodiments, is indocyanine green ("ICG"). ICG is commercially available from, for example, Akorn, Inc. (Buffalo Grove, Ill.), which sells it under the name IC-GREEN™. In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The dyes may be mixed or combined. In some embodiments, dye analogs may be used. A "dye analog" is a dye that has been chemically modified, but still retains its ability to fluoresce when exposed to radiant energy of an appropriate wavelength. ICG, Fast Blue and Fluorogold have all been used in mammals with low evidence of neuronal toxicity and are preferred.

Preferably, the dye selected is one that has low toxicity and has excitation and emission peaks within the "optical window" of tissue, where absorption due to endogenous chromophores is low. Near infrared light can therefore penetrate tissue to a depth of several millimeters to a few centimeters. ICG is particularly preferred both because it has low toxicity and because it has been approved by the Food and Drug Administration for several diagnostic purposes in humans. Further, its absorption (excitation) and emission peaks (805 and 835 nm, respectively) lie within the "optical window" of tissue. After intravenous injection, ICG is bound within 1 to 2 seconds, mainly to globulins (1-lipoproteins), and remains intravascular, with normal vascular permeability. ICG is not metabolized in the body and is excreted exclusively by the liver, with a plasma half-life of 3 to 4 minutes. It is not reabsorbed from the intestine and does not undergo enterohepatic recirculation. The recommended dose for ICG video angiography is 0.2 to 0.5 mg/kg; the maximum daily dose should not exceed 5 mg/kg.

For intraoperatively visualizing lymph nodes in areas of interest, the surgical field, or the portion of the surgical field in which imaging is desired, is illuminated with a light of the excitation wavelength or wavelengths suitable for the dye or dyes used. Ambient light may need to be dimmed to permit the fluorescence to be seen. Observation will typically also require magnification. Where the excitation wavelength is outside of the visible range (where, for example, the excitation wavelength is in the ultraviolet or near infrared range), the light source may be designed to permit switching or "toggling" between the excitation wavelength and visible light. This permits the practitioner to note the position of the tissue of interest using the fluorescent property in relation to the rest of the surgical field and surrounding (but non-fluorescent) structures.

The dye is typically administered by a bolus injection to permit visualizing the lymph nodes draining the bladder. If the time for surgery is expected to be long, or if the practitioner desires to increase the intensity of fluorescence during the procedure, a continuous injection or one or more further injections can be made to keep levels relatively high during the operation.

Typically, the dye will be administered preoperatively, to permit the dye to drain from the bladder to the lymph nodes prior to commencing the operation. As noted, in animal studies, SLNs were successfully visualized in animals in which ICG was instilled at 10, 20, 30, or 60 minutes before intraoperative imaging. Since cystectomy procedures can take several hours, the time needed to perform the portions of the operation that will occur before identifying the sentinel lymph nodes may be taken into account in determining when to administer the dye to the bladder.

Animal studies demonstrated drainage satisfactory to permit visualization of SLN in as little as 10 minutes, with the dye lasting long enough to visualize the SLN over an extended period. The studies showed that unilateral tumors on the ipsilateral side resulted in more and quicker drainage to the SNL than did unilateral tumors on the contra lateral side, but these differences were not great enough to affect the timing of dye administration. Administration of dye shortly before the start of or even during the operation will result in the presence of sufficient dye in the SNL for ready visualization.

Occasionally, a patient presents with significant abdominal adhesions from previous procedures or other complicating factors that extend the duration of the operation significantly over the norm. An administration of dye shortly before the start of the operation is expected to provide sufficient fluorescence to visualize the SNL. If the bladder has not been resected or removed within two hours of dye administration, however, more dye can be instilled into the bladder and a 10 minute interval provided to allow for dye uptake and transport, thus increasing the amount of dye in the SNL before the bladder resection or removal. The practitioner can readily determine whether or not additional dye administration is warranted prior to bladder resection or removal by exposing the surgical area to illumination with the appropriate peak excitation frequency of the dye being used, visualizing at the appropriate peak emission frequency, and determining whether at least some lymph nodes are showing fluorescence.

The dye may be administered in the patient's room before the patient is taken to the operating room to minimize waiting in the operating room while the dye is transported from the bladder to the lymph nodes. Alternatively, the dye can be administered in the operating room before or even during the operation. The intravesical instillation of the dye may be performed immediately before preparation and draping of the patient. Given preparation and incision times, that protocol would typically leave at least 15 minutes for dye transfer before incision, and an additional 15 minutes before lymphadenectomy begins. If the dye is administered preoperatively, it is desirable that the dye not be administered too long before surgery for it to be present in the lymph nodes in sufficient quantities to permit adequate intraoperative visualization of the lymph nodes. Typically, it is preferable that the dye is administered within 4, 3, or 2 hours of commencement of surgery, with each shorter one of these times being more preferred. More preferably, the dye is administered from 1-2 hours before surgery, and still more preferably, less than an hour before surgery. Still more preferably, the dye is administered when the patient is prepped and draped. The dye can also be administered during the surgery, preferably 10 minutes or more before the practitioner intends to commence identifying the location of SLN or involved nodes.

Where intramural injection is elected, a long needle is introduced to the bladder lumen transurethrally with a cystoscope and is used to inject dye into the lesion stalk or edges of a previous resection or scar. Typically, such injections are made by visualizing the tumor through a camera attached to or contained in the cystoscope (an endoscope). For intramural injections, the injections are preferably made within 5, 4, 3, or 2 hours or within 1 hour of commencement of surgery, with each shorter one of these times being more preferred. Administration of dye approximately 10-15 minutes before the start of surgery (first incision) is preferred.

The maximum daily dosage of ICG for adults is 2 mg/kg. There is no data available describing the signs, symptoms, or laboratory findings accompanying an overdose of ICG. The $LD_{50}$ after IV administration ranges between 60 and 80 mg/kg in mice, 50 and 70 mg/kg in rats, and 50 to 80 mg/kg in rabbits.

EXAMPLES

Example 1

UPII-SV40T transgenic mice were used that express the SV40 T antigen specifically in the urothelium and that reliably develop bladder tumors. Twelve female mice received intravesical instillations of ICG (2.5 mg/mf, 100 or 200 µl) and 20, 30 and 60 minutes later underwent intraoperative near infrared fluorescence ("NIRF") identification of lymphatic channels and SLNs. Wildtype female mice were controls. NIRF and H&E microscopy were used to confirm presence of the lymphatic tissue and eventual metastasis.

All 12 animals receiving ICG showed draining lymphatic channels and SLNs. At least two sentinel nodes were detected in all animals. SLNs were in common or external iliac lymphatic chains. In one mouse, SLNs were detected in presacral and paravesical chain. SLNs were not visible in normal saline control group. IRF and H&E microscopy confirmed presence of lymphatic tissue in resected SLNs.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying a lymph node draining the bladder of a patient with bladder cancer, comprising: (a) instilling into a lumen of the patient's bladder a dye, dissolved in solution, which fluoresces at an emission wavelength when said dye is contacted with an excitation wavelength; (b) allowing the dye to be taken into the bladder and drain to said lymph node; (c) exposing the lymph node to a source of illumination comprising said excitation wavelength under conditions such that fluorescent dye in the lymph node fluoresces; and (d) detecting the presence of fluorescence of said dye in said lymph node, wherein the presence of fluorescence indicates that the lymph node is draining said bladder.

2. The method of claim 1, wherein said dye is administered through a cystoscope, endoscope, or catheter.

3. The method of claim 1, wherein said lymph node detecting of step (d) is by visualizing fluorescence of said lymph node on a image display.

4. The method of claim 1, wherein said exposing of said lymph node to said illumination comprising said excitation wavelength is by a laparoscopic instrument.

5. The method of claim 1, wherein said dye is a near infrared dye.

6. The method of claim 1, wherein said dye is a tricarbocyanine dye or an analog thereof.

7. The method of claim 6, wherein the tricarbocyanine dye is indocyanine green.

8. The method of claim 1, wherein the subject is a human.

9. The method of claim 1, wherein said instillation of step (a) is performed during a radical cystectomy.

10. The method of claim 1, wherein said instillation of dye of step (a) is performed within 4 hours of commencing a radical cystectomy.

* * * * *